US006388145B1

(12) United States Patent
Kustov et al.

(10) Patent No.: US 6,388,145 B1
(45) Date of Patent: *May 14, 2002

(54) METHOD FOR THE OXIDATION OF BENZENE AND/OR TOLUENE TO PHENOL AND/OR CRESOLS

(75) Inventors: Leonid Modestovich Kustov; Andrei Leonidovich Tarasov; Aleksandr Arunovich Tyrlov; Viktor Ignatyevich Bogdan, all of Moscow (RU)

(73) Assignee: General Electric Company, Schenectady, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/533,739

(22) Filed: Mar. 23, 2000

(30) Foreign Application Priority Data

Apr. 5, 1999 (RU) .............................. 99106881

(51) Int. Cl.$^7$ .............................................. C07C 37/00
(52) U.S. Cl. ...................................................... 568/800
(58) Field of Search ........................................ 568/800

(56) References Cited

U.S. PATENT DOCUMENTS

| | | |
|---|---|---|
| 4,367,358 A | 1/1983 | Kaeding |
| 4,559,314 A | 12/1985 | Shihabi |
| 4,581,215 A | 4/1986 | Kaeding |
| 4,724,270 A | 2/1988 | Chang et al. |
| 4,950,829 A | 8/1990 | Han et al. |
| 4,975,402 A | 12/1990 | Le Van Mao et al. |
| 4,982,013 A | 1/1991 | Gubelmann et al. |
| 5,001,280 A | 3/1991 | Gubelmann et al. |
| 5,055,623 A | 10/1991 | Gubelmann et al. |
| 5,110,995 A | 5/1992 | Kharitonov et al. |
| 5,672,777 A | 9/1997 | Kharitonov et al. |
| 5,808,167 A | 9/1998 | McGhee |
| 5,849,257 A | 12/1998 | Fujiwara et al. |
| 5,892,132 A | 4/1999 | Rooks et al. |
| 6,255,539 B1 | 7/2001 | Uriarte et al. |

FOREIGN PATENT DOCUMENTS

| | | |
|---|---|---|
| DE | 19634406 | 3/1998 |
| EP | 0 068 755 A2 | 1/1983 |
| EP | 0 134 331 A1 | 3/1985 |
| EP | 0302636 A1 | 2/1989 |
| EP | 0568913 A2 | 11/1993 |
| EP | 889 018 | 1/1999 |
| JP | 56-77234 | 6/1981 |
| JP | 56-87527 | 7/1981 |
| JP | 9-194412 | 7/1997 |
| WO | WO 95 27560 | 10/1995 |
| WO | WO 95/27691 | 10/1995 |
| WO | 98/25698 | 6/1998 |

OTHER PUBLICATIONS

*Selective Oxidation of Fluorobenzenes on Modified Zeolites Using N2O as an Oxidant.* Bogdan, V.I.; Kustov, L.M.; Batizat, D.B.; Sakharov, A.M.; Kazansky, V.B. (N.D. Zelinsky Institute Organic Chemistry, Russian Academy Sciences, Moscow, 117334, Russia). Stud. Surf. Sci. Catal., 94 (Catalysis by Microphorous Materials), 635–40 (English) 1995.

*NOx Adsorption Complexes on Zeolites Containing Metal Cations and Strong Lewis Acid Sites and Their Reactivity in CO and $CH_4$ Oxidation: A Spectroscopic Study.* Kustov, L.M., Smekalina, E.V.; Uvarova, E.B.; Kazansky, V.B. (N.D. Zelinsky Institute Organic Chemistry, Russian Academy Sciences, Moscow, 117334, Russia). Stud. Surf. Sci. Catal., 97 (Zeolites: A Refined Tool for Designing Catalytic Sites), 409–15 (English) 1995.

*The Role of Lewis Acid Sites in Adsorption and Activation of Oxygen in Redox Type Reactions on Zeolites.* Zholobenko, V.L.; Kustov, L.M., Kazansky, V.B. (N.D. Zelinsky Institute of Organic Chemistry, Russian Academy Sciences, Moscow 117334, Russia). Proc. Int. Zeolite Conf., 9$^{th}$, Meeting Date 1992, vol. 2, 299–307. Editor(s): Von Ballmoos, Ronald; Higgins, John B.; Treacy, Michael M. J. Butterworth–Heinemann: Boston, Mass. (English) 1993.

*Study of Active Centers for Oxidation of Benzene and Formation of Cation–Radicals in H–ZSM–5 Zeolites and H–Mordenite.* Zholobenko, V.L.; Kustov, L.M.; Kazanskii, V.B. (Inst. Org. Khim. Im. Zelinskogo, Moscow, USSR. Kinet, Katal., 30(4), 901–5 (Russian) 1989. (Translation).

*Catalytic Activity and Active Sites in Zeolite Catalysts for N2O Decomposition.* Uvarova, E.B.; Stakeev, S.A.; Kustov, L.M.; Brei, V.V. (N. D. Zelinsky Institute Organic Chemistry, Russian Academy Sciences, Moscow, Russia). Stud. Surf. Sci. Catal., 98(Zeolite Science 1994: Recent Progress and Discussions) 148–9 (English) 1995.

*Radical Intermediates in the Photoinduced Formation of Benzene Cation–Radicals over H–ZSM–5 Zeolites,* V.A.Bolshov, A.M. Volodin, G.M. Zhidomirov, A.A. Shubin and A.F. Bedilo, Boreskov Institute of Catalysis, Siberian Branch of the Russian Academy of Sciences, Novosibirsk 630090, Russia, Received: Nov. 29, 1993, In Final Form: May 10, 1994., J. Phys. Chem 1994, 98, pp. 7551–7554; 1994 American Chemical Society.

(List continued on next page.)

Primary Examiner—Michael L. Shippen

(57) ABSTRACT

The invention relates to the field of organic synthesis, more specifically to a method for the production of phenol and cresol by the direct selective oxidation of benzene and toluene with nitrous oxide in the presence of a heterogeneous catalyst. Commercial high-silica zeolites are first calcined at a temperature of 500–950° C. sufficient to dehydroxylate it. It is then modified by the addition of modifying agents—zinc ions or zinc oxide—by applying a zinc compound to it. The catalyst is then activated in air or an inert gas at 300–850° C. The mixture of benzene or toluene with the nitrous oxide is brought into contact with the modified catalyst at 225 to 500° C.

6 Claims, No Drawings

OTHER PUBLICATIONS

"One–Step Benzene to Phenol (BTOP)" (literature), Marcos A. Cesar, 1998 PEP Client Conference, Redwood Shores, CA. May 2–5, 1998.

"One–Step Phenol Process Offers Higher Yield", Chementator, Edited by Ken Fouhy. Chemical Engineering/Feb. 1997, p. 15.

"New Catalyst Softens Conditions for Bisphenol–A Production", Chementator, Edited by Ken Fouhy. Chemical Engineering/Feb. 1997, p. 15.

Sobolev, V., "Catalytic Properties of ZSM–5 Zeolites in $N_2O$ Decomposition: The Role of Iron", Journal of Catalysis, 139, p. 435–43 (1993).

Kharitonov, A.S., "Ferrisilicate Analogs of ZSM–5 Zeolite as Catalysts For One–Step Oxidation of Benzene to Phenol", Applied Catalysis, 98, p. 33–43 (1993).

Panov, G.I., "Oxidative Hydroxylation Using Dinitrogen Monoxide: A Possible Route for Organic Synthesis Over Zeolites", Applied Catalysis, 98, 1–20 (1992).

Volodin, A., J., "The Role of Surface $\alpha$–Oxygen in Formation of Cation Radicals at Benzene Adsorption on ZSM–5", Phys. Chem 1994, 98, 7548–7550.

Uriarte, Anthony K., "Direct Hydroxylation of Benzene to Phenol by Nitrous Oxide", $3^{rd}$ World Congress on Oxidation Catalysis, Sep. 21–26, 1997.

Zholobenko, V., "Preparation of Phenol over Dehydroxylated HZSM–5 Zeolites", Mendeleev Commun. 1993, p. 28–29.

Iwamato, et al., "Catalytic Oxidation by Oxide Radical Ions", J. Phys. Chem., 1983, V. 87, No. 6, p. 903.

PCT International Search Report for International Application No. PCT/US 00/08925, International Filing date Apr. 4, 2000.

METHOD FOR THE OXIDATION OF BENZENE AND/OR TOLUENE TO PHENOL AND/OR CRESOLS

BACKGROUND OF THE INVENTION

The present application is a U.S. non-provisional application based upon and claiming priority from Russian Application No. 99106881 which is hereby incorporated by reference.

The proposed invention relates to the field of organic synthesis, more specifically to a method for the production of phenol and cresol by the direct selective oxidation of benzene and toluene by means of a gaseous mixture containing nitrous oxide $N_2O$ in the presence of a heterogeneous catalyst. The catalysts used are zeolite-containing catalysts modified by special treatment and additives.

The known method most similar to the proposed method is a means of oxidizing benzene and/or toluene to phenol and/or cresols using nitrous oxide as the oxidizing agent, with a heterogeneous catalyst containing a high-silica pentasil zeolite which is modified in a preliminary step in which metal ion promoters are added by applying a compound of metals such as iron, etc. to it, then activating the catalyst at a high temperature between 300 and 500° C., and bringing the benzene and/or toluene and the nitrous oxide into contact with the modified heterogeneous catalyst at a reaction temperature between 275 and 450° C. (U.S. Pat. No. 5,110,995, IPC C 07 C 37/60, national code 568/800, 1992).

In the known method, pentasil zeolites (ZSM-5, ZSM-11, ZSM-12, ZSM-23), mordenite, H-beta zeolite and EU-1 that have been modified with small amounts of iron ions at the zeolite synthesis stage have been shown to be highly active in the direct oxidation of benzene to phenol. At temperatures of 400–450° C. and a contact time of 2–4 sec (space velocity in terms of benzene 0.4 $h^{-1}$) and a benzene:$N_2O$ molar ratio of 1:4, the yield of phenol reaches values of 20–30% with a selectivity of 90–97%. Other systems modified with transition metal ions (Mn, Co, Ni, V, Cu), have been shown to be less active than iron-containing zeolites.

The disadvantages of the known method are related to the need to introduce the iron into the zeolite and to control the state of the iron ions, the low value of the space velocity in benzene and the quite lengthy contact time necessary to achieve acceptable, but not especially high yields of the final products, as well as the low selectivity achieved at elevated temperatures.

The result produced by the proposed method is an increase in the yield of the final products and an improvement in the selectivity and activity of the catalyst achieved by creating strong Lewis acid sites in the zeolite.

BRIEF SUMMARY OF THE INVENTION

According to this method, a starting material such as benzene or toluene or a combination thereof is oxidized to form phenol, creosols or a combination thereof. The oxidation is performed at a temperature of 225° C. to 500° C. in the presence of a zeolite catalyst and an oxidizing agent which comprises nitrous oxide. The zeolite catalyst is treated according to a special procedure to form the catalyst. Specifically, the zeolite is first calcined at 500–950° C. in air or at 300–850° C. in an inert gas. Next, the zeolite is impregnated with Zn ions by ion exchange or by exposing it to an aqueous solution of zinc salt. Last, the impregnated zeolite is heated in air or an inert gas to a temperature of 300–850° C.

DETAILED DESCRIPTION OF THE INVENTION

As the high-silica zeolite one can use a pentasil; the pentasil may be the H form of the ZSM-5 zeolite with an Si/Al ratio of 10 to 200.

The reagents maybe taken in a ratio of $N_2O$:benzene and/or toluene from 1:7 to 10:1.

Furthermore, the mixture of benzene and/or toluene with nitrous oxide may be diluted with an inert gas—nitrogen and/or argon and/or helium.

Furthermore, the heterogeneous catalyst may be used mixed with a binder in the form of silica gel or alumina.

The method for oxidizing benzene and/or toluene to phenol and/or cresols is accomplished as follows.

The starting materials for the catalyst are commercial forms of the zeolite are:

(1) the high-silica zeolite ZSM-5
(2) H-beta zeolite

Commercial zeolite ZSM-5, advantageously with a Si/Al ratio greater than 10 and preferably with a ratio of 40–100, is used. ZSM-5 zeolite is modified with compounds containing Zn ions by ion exchange from nitrates, chlorides and other salts of zinc, or by impregnating it with aqueous solutions of zinc salts. In a preliminary step the zeolite is calcined at 400–950° C. in air or an inert gas (under static conditions or in a flow). The indicated temperature ensures the dehydroxylation of the zeolite. The zeolite is then impregnated with an aqueous solution of zinc nitrate with a normality of 0.1N to 2N in an amount sufficient to add zinc oxide at a rate of from 0.1 to 10 wt %.

After impregnation, the zeolite is activated at a temperature of 300–500° C.

This impregnation process may be accomplished in one step or in several steps with intermediate activation at 500–700° C.

Acidic forms of the zeolite may be used to prepare the catalyst. The acidic H form of the high-silica zeolite may be prepared by ion-exchange of the Na form of the zeolite with an aqueous solution of an ammonium salt, a nitrate or chlorite or by treating the Na form of the zeolite with an aqueous solution of an inorganic or an organic acid.

The degree of ion exchange of sodium by ammonia or a proton is from 30 to 100% (most preferable is 50–b 95%). The Na form of the zeolite can also be used as a starting material for preparing the zeolite containing Zn.

The zeolite is used as a catalyst, either in the pure form or combined with a binder. Amorphous silica gel with a specific surface area of 100–600 $m^2/g$ or alumina (100–400 $m^2/g$) or a mixture thereof is used as the binder. The content of binder in the catalyst is from 5 to 50 wt %, preferably 20–30%.

Nitrous oxide is used either pure, or in a mixture with an inert gas—nitrogen or helium. Aromatic hydrocarbons—benzene and toluene—are used as the substrates for the selective oxidation to phenol and cresols. The substrate is introduced at a rate to give a mixture with $N_2O$ having a molar ratio of $N_2O$:substrate from 1:7 to 5:1, preferably from 1:2 to 4:1. The space velocity for the substrate is from 0.2 to 5 $h^{-1}$, ordinarily 0.5–2 $h^{-1}$. The reaction proceeds at a temperature of 225–500° C. The contact time of the reaction mixture with the catalyst is 0.5–8 sec, normally 1–4 sec. The gases exiting from the reactor are a mixture of the corresponding phenols and heavy products that are separated and analyzed by analytical methods. The catalyst may be easily and reversibly regenerated by calcining at 400–600° C. in a flow of air, oxygen, nitrous oxide, or in a mixture of these gases in inert gas for a period of 1–3 hours.

EXAMPLES

Example 1

10 grams of HZSM-5 zeolite are calcined at 900° C. in a flow of air for 3 hours and are modified by being impregnated to the zeolite's moisture-holding capacity with an aqueous solution of 1N zinc nitrate. The amount of zinc nitrate added amounts to 2 wt % zinc oxide, obtained on decomposition. The resulting zeolite is then activated at 780° C. for 2 hours to convert the nitrate to zinc oxide in the zeolite channels. 1 gram of catalyst with 2% ZnO/HZSM-5 (Si/Al=21), particle size 0.2–0.5 mm, is mixed with 1 gram of quartz of the same particle size and placed in a quartz or steel reactor, i.d. 7 mm. Prior to reaction, the catalyst is activated in an air flow (60 ml/min) at a temperature of 450° C. for 1 h. The reaction is run under the following conditions: T=450° C., $N_2O:C_6H_6$=1:1, space velocity of benzene V=0.3 $h^{-1}$.

Example 2

The catalyst was prepared as in Example 1. The reaction was run at T=440° C., $N_2O:C_6H_6$ 0.5:1, V=0.5 $h^{-1}$. The yield of phenol was 39% with a selectivity of 98%.

Example 3

The catalyst was prepared as in Example 1, except that the HZSM-5 catalyst was activated at 600° C. The reaction was run at T=440° C., the benzene was delivered at V=0.5 $h^{-1}$ at a molar ratio $N_2O:C_6H_6$=0.5:1. The yield of phenol was 35% with a selectivity of 99%.

Example 4

The catalyst was prepared as in Example 1, except that the catalyst used and the calcining temperature required to dehydroxylate the starting H form of the zeolite differed. The zeolite used was 2% ZnO/H-beta (Si/Al=25) and it was calcined at 800° C. Reaction conditions: V=1.7 $h^{-1}$, $N_2O:C_6H_6$=1:7. The results are shown in Table 1.

TABLE 1

Yield of phenol from benzene oxidized over 2% ZnO/H-beta zeolite
(calculated for $N_2O$)
(V = 1.7 $h^{-1}$, $N_2O:C_6H_6$ = 1.7)

| Catalyst | Reaction temperature, ° C. | | |
|---|---|---|---|
|  | 420 | 440 | 460 |
| ZnO/H-beta | 27.3 | 38.5 | 38.0 |

Example 5

Catalyst prepared as in Example 1 is loaded into a 1-cm³ reactor (particle size 1–2 mm). Toluene is delivered at V=0.25 $h^{-1}$ at a molar ratio of $N_2O$:toluene=1:1. The reaction temperature is 425° C., the yield of a mixture of o-, m-, p-cresols is 21.1% with selectivity for cresol of 75%. Benzene, xylene, and phenol are the major by-products. The ratio of o-, m-, and p-cresols is 30:40:30.

The examples cited above of the use of a Zn-containing high-silica zeolite catalyst in the oxidation of benzene and toluene to the corresponding phenols with nitrous oxide being used as the oxidizing agent demonstrate the following advantages compared to known catalysts:

1) The rate of conversion over the given catalyst may be increased to 50–77% with no reduction in selectivity (98–100%).

2) The stability of the catalyst is increased by adding zinc ions or zinc oxide, which act as strong Lewis acids, to HZSM-5 zeolite.

3) High activity and selectivity are achieved in the oxidation of toluene by nitrous oxide over Zn-containing zeolite catalyst.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out the this invention, but that the invention will include all embodiments falling within the scope of the appended claims.

What is claimed is:

1. A method for oxidizing a starting material selected from the group consisting of benzene, toluene and combinations thereof, to an oxidation product selected from the group consisting of phenol, creosols and combinations thereof, wherein the oxidizing agent comprises nitrous oxide, and said oxidation is performed in the presence of a zeolite catalyst wherein the catalyst is prepared by a process comprising the steps of:

a) calcining a zeolite at a temperature of from 500–950° C. in air or at 300–850° C. in an inert gas, b) impregnating the zeolite with Zn ions by ion exchange or by exposing the zeolite to an aqueous solution of a zinc salt, and c) activating the impregnated zeolite by heating it in air or an inert gas to a temperature of 300–850° C., wherein the reaction is performed by contacting the starting material with the catalyst in the presence of nitrous oxide at a temperature of 225 to 500° C.

2. A method according to claim 1, wherein pentasil is used as the high-silica zeolite.

3. A method according to claim 1, wherein the pentasil is the H form of ZSM-5 zeolite with an Si/Al ratio of from 10 to 200.

4. A method according to any of claim 1, wherein the reagents are taken at a ratio of $N_2O$:benzene and/or toluene from 1:7 to 10:1.

5. A method according to claim 1, wherein the mixture of benzene and/or toluene with the nitrogen oxide is diluted with an inert gas—nitrogen and/or argon and/or helium.

6. A method according to claim 1, wherein the heterogeneous catalyst is used in a mixture with a binder in the form of silica gel or alumina.

* * * * *